(12) United States Patent
Takaya

(10) Patent No.: US 10,052,399 B2
(45) Date of Patent: Aug. 21, 2018

(54) COMPOSITION, SUPPORT, WASTEWATER TREATMENT SYSTEM, WASTEWATER TREATING METHOD, DEODORIZATION METHOD, AND BATCH WASTEWATER TREATING METHOD

(71) Applicant: JAPAN ENVIRONMENTAL SCIENCE COMPANY, Tokyo (JP)

(72) Inventor: Makoto Takaya, Tokyo (JP)

(73) Assignee: JAPAN ENVIRONMENTAL SCIENCE COMPANY, Tokyo (JP)

( * ) Notice: Subject to any disclaimer, the term of this patent is extended or adjusted under 35 U.S.C. 154(b) by 0 days.

(21) Appl. No.: 15/505,427

(22) PCT Filed: Aug. 25, 2015

(86) PCT No.: PCT/JP2015/073815
§ 371 (c)(1),
(2) Date: Feb. 21, 2017

(87) PCT Pub. No.: WO2016/031804
PCT Pub. Date: Mar. 3, 2016

(65) Prior Publication Data
US 2017/0266332 A1    Sep. 21, 2017

(30) Foreign Application Priority Data

Aug. 25, 2014  (JP) ................. 2014-171005
Aug. 25, 2014  (JP) ................. 2014-171006

(51) Int. Cl.
| A61L 9/01 | (2006.01) |
| C12N 1/20 | (2006.01) |
| C02F 3/34 | (2006.01) |
| C02F 101/32 | (2006.01) |
| C02F 103/32 | (2006.01) |

(52) U.S. Cl.
CPC .............. *A61L 9/01* (2013.01); *C02F 3/341* (2013.01); *C02F 3/343* (2013.01); *C12N 1/20* (2013.01); *C02F 2101/32* (2013.01); *C02F 2103/32* (2013.01)

(58) Field of Classification Search
CPC ... A61L 9/01; A61L 9/011; C12N 1/20; C02F 2101/32; C02F 3/341; C02F 3/343; C02F 2103/32; C02F 3/3411; C07G 11/00; C12P 1/04
See application file for complete search history.

(56) References Cited

FOREIGN PATENT DOCUMENTS

| CN | 102212493 A | 10/2011 |
| JP | 3236771 | 10/1991 |
| JP | 2553727 B2 | 11/1996 |
| JP | 10295367 | 11/1998 |
| JP | H11179396 A | 7/1999 |
| JP | 2001104991 A | 4/2001 |
| JP | 2001129580 A | 5/2001 |
| JP | 2004275960 A | 10/2004 |
| JP | 2005185658 A | 7/2005 |
| JP | 2012232905 A | 11/2012 |
| WO | WO-2010/059028 A1 | 5/2010 |

OTHER PUBLICATIONS

International Search Report and Written Opinion for Application No. PCT/JP2015/073815, dated Nov. 17, 2015.
Sumio Akiyama, Yushi, 1991, vol. 44, No. 10, pp. 46-51, ISSN 0912-5396.
European Search Report for Application No. 15835441.5, dated Jun. 27, 2017.
English Translation of Japanese Office Action for Application No. 2016-545539, dated Mar. 28, 2017.

*Primary Examiner* — Debbie K Ware
(74) *Attorney, Agent, or Firm* — Marshall, Gerstein & Borun LLP

(57) ABSTRACT

Provided are a composition containing as active ingredients thereof *Bacillus subtilis* strain BN1001 (deposit number: NITE BP-02608 and *Bacillus subtilis* var. *natto*, a wastewater treatment system provided with a biological treatment tank that biologically treats wastewater wherein the *Bacillus subtilis* strain BN1001 and *Bacillus subtilis* var. *natto* are contained in the biological treatment tank, a wastewater treating method that biologically treats wastewater comprising a step for adding the *Bacillus subtilis* strain BN1001 and *Bacillus subtilis* var. *natto* to the wastewater, a deodorization method comprising a step for contacting the *Bacillus subtilis* strain BN1001 and *Bacillus subtilis* var. *natto* with a malodorous source, a support having *Bacillus subtilis* and *Bacillus subtilis* var. *natto* supported thereon, a wastewater treatment system wherein the support is contained in a biological treatment tank, a wastewater treating method comprising a step for adding the support to wastewater, and a batch water treating method wherein the support is contained in a biological treatment tank.

12 Claims, 4 Drawing Sheets

COMPOSITION, SUPPORT, WASTEWATER TREATMENT SYSTEM, WASTEWATER TREATING METHOD, DEODORIZATION METHOD, AND BATCH WASTEWATER TREATING METHOD

CROSS-REFERENCE TO RELATED APPLICATION

The present application is the US national phase of International Application No. PCT/JP2015/073815, filed on Aug. 25, 2015, which claims priority to Japanese Patent Application No. 2014-171005, filed Aug. 25, 2014, and Application No. 2014-171006, filed Aug. 25, 2014. The priority applications JP 2014-171005 and JP 2014-171006, are hereby incorporated by reference.

TECHNICAL FIELD

The present invention relates to a composition, support, wastewater treatment system, wastewater treating method, deodorization method and batch wastewater treating method.

BACKGROUND ART

The wastewater discharged from commercial kitchens of restaurants and other members of the restaurant industry as well as food plants, processed food plants and other factories contains large amounts of fats and oils, starch, proteins and other contaminants. In particular, the concentrations of fats and oils in wastewater have increased in recent years due to changes in customer needs. Consequently, wastewater treatment is becoming essential at facilities and establishments discharging such wastewater.

Wastewater is typically treated using an activated sludge method. However, activated sludge methods suffer a decrease in treatment capacity of the biological treatment tank as the fat and oil concentration of the wastewater increases. Consequently, wastewater is pretreated using devices such as a pressure flotation device. However, the use of a pressure floatation device requires the use of flocculants and other chemicals and results in the generation of sludge. Therefore, numerous businesses using these devices are burdened with device installation and maintenance costs, chemical costs and sludge treatment costs.

In Japan, all commercial kitchens are required to install grease traps. Grease traps refer to water storage tanks in which the inside of the tank is divided into a plurality of compartments, and are equipped with a water inlet for introducing wastewater and a drain outlet for discharging wastewater to prevent fats and oils present in wastewater from running off directly into the sewer by trapping fats and oils in a trap. Neglecting to clean the grease trap not only results in the generation of a foul odor, but is also unsanitary due to accumulation of fats and oils, sludge and scum. However, the work of cleaning the grease trap is labor-intensive and becomes a burden for many businesses.

In view of these circumstances, attempts have been made to improve the efficiency of wastewater treatment using microorganisms. For example, Patent Document 1 describes a method for degrading oils and reducing levels of n-hexane extracted substances by adding live cultured bacteria and live bacterial preparation of *Bacillus subtilis* strain BN1001, deposited as Accession No. NITE BP-02608 with NITE Patent Microorganisms Depository of the National Institute of Technology and Evaluation, located at #122 2-5-8 Kazusakamatari, Kisarazu-shi, Chiba 292-0818, Japan, to oil-containing wastewater.

DISCLOSURE OF THE INVENTION

Problems to be Solved by the Invention

However, there are cases in which the use of *Bacillus subtilis* strain BN1001 alone is not sufficient for improving the efficiency of wastewater treatment.

Therefore, an object of the present invention is to provide a composition capable of further improving the degradation efficiency of oils and fats, starch and proteins to further improve the efficiency of wastewater treatment and deodorization. In addition, an object of the present invention is to provide a support on which is supported a group of microorganisms capable of improving the degradation efficiency of oils and fats, starch and proteins to further improve the efficiency of wastewater treatment and deodorization by adding to a biological treatment tank of a wastewater treatment system. Moreover, an object of the present invention is to provide a wastewater treatment system having improved treatment capacity and a wastewater treating method having improved treatment capacity. In addition, an object of the present invention is to provide a highly efficient deodorization method. Moreover, an object of the present invention is to provide a batch wastewater treating method having improved treatment capacity.

Means for Solving the Problems

The present invention is as indicated below.

(1) A composition containing as active ingredients thereof *Bacillus subtilis* strain BN1001 (deposited as Accession No. NITE BP-02608) and *Bacillus subtilis* var. *natto*.

(2) The composition described in (1), which is a powder.

(3) The composition described in (1), which is a liquid.

(4) The composition described in any of (1) to (3), which is for degrading oils and fats.

(5) The composition described in any of (1) to (3), which is for degrading starch.

(6) The composition described in any of (1) to (3), which is for degrading protein.

(7) The composition described in any of (1) to (3), which is for treating wastewater.

(8) The composition described in any of (1) to (3), which is for deodorization.

(9) A wastewater treatment system provided with a biological treatment tank that biologically treats wastewater; wherein, the composition described in (1) is contained in the biological treatment tank.

(10) A wastewater treating method that biologically treats wastewater, comprising a step for adding the composition described in (1) to the wastewater.

(11) A deodorization method comprising a step for contacting the composition described in (1) with a malodorous source.

(12) A support having *Bacillus subtilis* strain BN1001 (deposited as Accession No. NITE BP-02608) and *Bacillus subtilis* var. *natto* supported thereon.

(13) A wastewater treatment system provided with a biological treatment tank that biologically treats wastewater; wherein, the support described in (12) is contained in the biological treatment tank.

(14) A wastewater treating method that biologically treats wastewater; comprising a step for adding the support described in (12) to the wastewater.

(15) A batch wastewater treating method, comprising: a wastewater introduction step for introducing wastewater into a biological treatment tank that biologically treats wastewater, an aeration step for aerating the introduced wastewater, a standing step for allowing the wastewater to stand undisturbed following aeration, and a discharge step for discharging the treated water after standing; wherein, each of the wastewater introduction step, the aeration step, the standing step and the discharge step is repeated, and the biological treatment tank contains the support described in (12).

Effects of the Invention

According to the present invention, a composition can be provided that is capable of further improving the degradation efficiency of fats and oils, starch and proteins to further improve the efficiency of wastewater treatment and deodorization. In addition, according to the present invention, a support having a group of microorganisms supported thereon can be provided that is capable of further improving the degradation efficiency of fats and oils, starch and proteins to further improve the efficiency of wastewater treatment and deodorization by adding to a biological treatment tank of a wastewater treatment system. Moreover, a wastewater treatment system having improved treatment capacity and a wastewater treating method having improved treatment capacity can be provided. In addition, a highly efficient deodorization method can be provided. Moreover, a batch wastewater treating method can be provided that has improved treatment capacity.

BEST MODE FOR CARRYING OUT THE INVENTION

Figure 1:
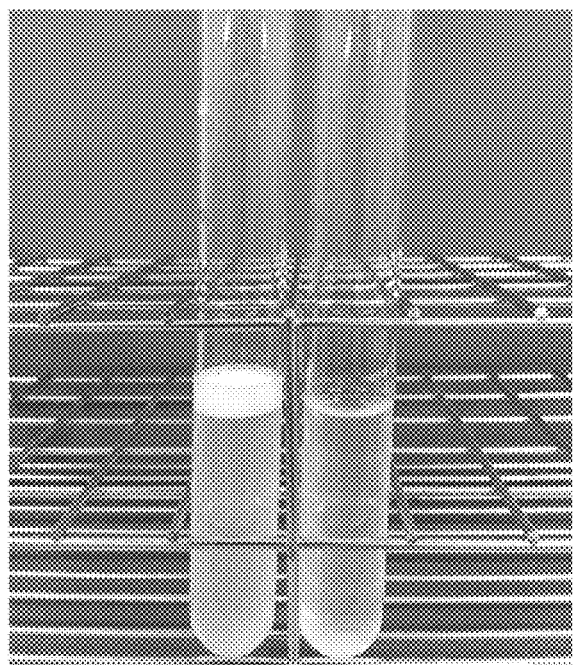
FIG. 1 is a photograph showing the results of a catalase activity test.

Although the following provides an explanation of preferable examples of the present invention, the present invention is not limited to these examples. Additions, omissions, substitutions and other changes can be made to the configuration of the present invention within a range that does not deviate from the gist thereof.

Composition

In one embodiment thereof, the present invention provides a composition containing as active ingredients thereof *Bacillus subtilis* strain BN1001 (deposited as Accession No. NITE BP-02608) and *Bacillus subtilis* var. *natto*.

As will be subsequently described, the aforementioned composition can be provided in the form of a powder or in the form of a liquid. Here, a powder includes forms such as a solid obtained by compression molding of a powder. In addition, a liquid includes forms having fluidity such as a liquid, gel or paste.

Regardless of whether in the form of a powder or liquid, the composition of the present embodiment may also contain a support, carbon source, nitrogen source or inorganic nutrient source and the like in addition to *Bacillus subtilis* strain BN1001 and *Bacillus subtilis* var. *natto*. In the case of being in liquid form, water is contained in addition to each of the aforementioned components.

Examples of the support include cellulose, activated charcoal, ceramics, polypropylene, porous carbon compositions, pearlite and calcium carbonate.

Examples of the carbon source include glucose, fructose, sucrose, maltose, lactose and starch.

Examples of the nitrogen source include amino acids, urea, peptones, bouillon, yeast extract, soy flour, soybean meal, cottonseed meal, corn stiplica, wheat bran, soy milk and beef extract.

Examples of inorganic nutrient sources include potassium chloride, magnesium sulfate, sodium chloride, potassium phosphate, calcium carbonate, vitamins and other trace elements.

*Bacillus subtilis* strain BN1001 and *Bacillus subtilis* var. *natto* are commercially available. *Bacillus subtilis* var. *natto* can be used without any particular limitations provided it is a microorganism classified as *Bacillus subtilis* var. *natto*. The proportion at which *Bacillus subtilis* strain BN1001 and *Bacillus subtilis* var. *natto* are present in the composition of the present embodiment is preferably from 10:90 to 90:10 and more preferably from 40:60 to 60:40.

In addition, although there are no particular limitations thereon provided the *Bacillus subtilis* strain BN1001 and *Bacillus subtilis* var. *natto* are contained to a degree to which the effects of the invention of the present application are demonstrated, the "containing as active ingredients" preferably refers to containing *Bacillus subtilis* strain BN1001 at 10% by weight to 90% by weight and *Bacillus subtilis* var. *natto* at 10% by weight to 90% by weight in terms of the dry weight thereof based on the total weight of all microorganisms contained in the composition, and more preferably refers to containing *Bacillus subtilis* strain BN1001 at 40% by weight to 60% by weight and *Bacillus subtilis* var. *natto* at 60% by weight to 40% by weight.

The composition of the present embodiment may be produced by mixing separately cultured *Bacillus subtilis* strain BN1001 and *Bacillus subtilis* var. *natto*, or may be produced from a culture broth obtained by culturing a mixture of *Bacillus subtilis* strain BN1001 and *Bacillus subtilis* var. *natto*. In addition, the composition of the present embodiment may also contain other microorganisms provided *Bacillus subtilis* strain BN1001 and *Bacillus subtilis* var. *natto* are contained as active ingredients. Examples of microorganisms other than *Bacillus subtilis* strain BN1001 and *Bacillus subtilis* var. *natto* include other *Bacillus subtilis* species, lactic acid bacteria and yeasts.

As will be subsequently described, for example, when the aforementioned composition is added to a biological treatment tank of a wastewater treatment system, the degradation efficiency of oils and fats, starch, proteins and other refractory components present in the wastewater improves considerably. As a result, treated water quality improves and the generation of foul odors and sludge decreases considerably.

As a result, the operation of a pressure floatation device, as is required in the case of treating wastewater having a high concentration of fats and oils, is no longer required. Consequently, chemicals required when using a pressure floatation device are also not required, and there is less susceptibility of the generation of sludge resulting from the use of a pressure floatation device. As a result, costs and labor required for wastewater treatment can be reduced considerably.

In addition to wastewater treatment, the composition of the present embodiment is also able to efficiently reduce foul odors by using at locations in the home or commercial facilities where foul odors are generated, such as the kitchen, food preparation areas, lavatory, bathroom, laundry room or garbage collection sites, as well as in barns located on pig farms or chicken farms. More specifically, the composition of the present invention is contacted with a malodorous source at these locations such as by sprinkling on the malodorous source. As a result, the foul odor can be eliminated by the microorganisms present in the composition efficiently degrading the causative substance of the foul odor or substances causing the generation thereof.

Examples of causative substances of foul odors include ammonia, methyl mercaptan, hydrogen sulfide, methyl sulfide, methyl disulfide, trimethylamine, acetaldehyde, propionaldehyde, n-butyraldehyde, isobutyraldehyde, n-valeraldehyde, isovaleraldehyde, isobutanol, ethyl acetate, methyl isobutyl ketone, toluene, styrene, xylene, propionic acid, n-butyric acid, n-valeric acid and isovaleric acid.

In this manner, according to the composition of the present embodiment, the efficiency of wastewater treatment and deodorization can be further improved by further improving the degradation efficiency of oils and fats, starch and proteins contained in wastewater.

Thus, the aforementioned composition is extremely useful as a composition for wastewater treatment. In addition, the aforementioned composition can also be said to be a composition for degrading fats and oils, a composition for degrading starch and a composition for degrading protein. In addition, the aforementioned composition can also be said to be a composition for deodorization.

The amount of the composition of the present embodiment used may be suitably adjusted while confirming such factors as the effect on wastewater treatment and the effect on deodorization.

Support

In one embodiment thereof, the present invention provides a support having *Bacillus subtilis* strain BN1001 (deposited as Accession No. NITE BP-02608) and *Bacillus subtilis* var. *natto* supported thereon.

Handling ease is improved by supporting the microorganisms on a support. In addition, although there are cases in which the microorganisms end up being washed away together with wastewater in the case of adding the microorganisms to a biological treatment tank, the supporting of the microorganisms on a support makes it easier for the microorganisms to become established in the biological treatment tank.

The support may be that used for a stationary bed system or fluidized bed system, or may be used for another type of system. A stationary bed system refers to a wastewater treatment system comprising immobilizing a support having microorganisms supported thereon in a biological treatment tank and then aerating from the lower portion thereof. A stationary bed system is superior in terms of adsorption of suspended solids (SS) and allows the obtaining of high-quality treated water.

A fluidized bed system refers to a wastewater treatment system comprising the addition of a support having microorganisms supported thereon to a biological treatment tank followed by allowing the support to flow using aeration or other form of stirring force. Since a fluidized support allows the obtaining of a large specific surface area, not only does it enable highly efficient contact with wastewater, there is little wear or damage to the support during operation, thereby resulting in superior durability.

There are no particular limitations on the support for a stationary bed system provided the support can be immobilized in a biological treatment tank, and examples thereof include a support in the form of a pouch, capsule or ball having a powdered support sealed therein, and a support in the form of a mesh, mesh ball or string.

There are no particular limitations on the support for a fluidized bed system provided the support is able to flow in a biological treatment tank, and examples thereof include supports in the form of a sponge or gel.

Factors such as the type of wastewater treatment, shape of the support, or amount of support used can be suitably selected corresponding to the properties and so forth of the wastewater treated by the wastewater treatment system.

In addition to *Bacillus subtilis* strain BN1001 and *Bacillus subtilis* var. *natto*, the support of the present embodiment may have a support, carbon source, nitrogen source or inorganic nutrient source and the like supported thereon. Examples of the *Bacillus subtilis* strain BN1001, *Bacillus subtilis* var. *natto*, support, carbon source, nitrogen source and inorganic nutrient source are the same as those contained in the composition of the present embodiment.

An example of a method used to support the microorganisms on the support consists of contacting the support with a culture broth obtained by culturing the microorganisms in a suitable medium. The aforementioned culture broth may be produced by mixing culture broths of separately cultured *Bacillus subtilis* strain BN1001 and *Bacillus subtilis* var. *natto*, or may be produced by culturing a mixture of *Bacillus subtilis* strain BN1001 and *Bacillus subtilis* var. *natto*.

The support of the present embodiment may have other microorganisms supported thereon provided the support contains *Bacillus subtilis* strain BN1001 and *Bacillus subtilis* var. *natto* as active ingredients. Examples of microorganisms other than *Bacillus subtilis* strain BN1001 and *Bacillus subtilis* var. *natto* include *Bacillus subtilis* species other than *Bacillus subtilis* strain BN1001, lactic acid bacteria and yeasts.

Here, although there are no particular limitations thereon provided the *Bacillus subtilis* strain BN1001 and *Bacillus subtilis* var. *natto* are contained to a degree to which the effects of the invention of the present application are demonstrated, the "containing as active ingredients" preferably refers to containing *Bacillus subtilis* strain BN1001 at 10% by weight to 90% by weight and *Bacillus subtilis* var. *natto* at 10% by weight to 90% by weight in terms of the dry weight thereof based on the total weight of all microorganisms supported on a support, and more preferably refers to containing *Bacillus subtilis* strain BN1001 at 40% by weight to 60% by weight and *Bacillus subtilis* var. *natto* at 60% by weight to 40% by weight.

As will be subsequently described, for example, when the aforementioned support is added to a biological treatment tank of a wastewater treatment system, the degradation efficiency of oils and fats, starch, proteins and other refractory components present in the wastewater improves considerably. As a result, treated water quality improves and the generation of foul odors and sludge decreases significantly.

As a result, the operation of a pressure floatation device, as is required in the case of treating wastewater having a high concentration of fats and oils, is no longer required. Consequently, chemicals required when using a pressure floatation device are also not required, and there is less susceptibility of the generation of sludge resulting from the use of a pressure floatation device. As a result, costs and labor required for wastewater treatment can be reduced considerably.

In addition, the support of the present embodiment is able to efficiently reduce foul odors generated by wastewater by adding to the biological treatment tank of a wastewater treatment system. This is the result of microorganisms present in the support efficiently degrading the causative substance of the foul odor or substances causing the generation thereof.

In this manner, according to the support of the present embodiment, the efficiency of wastewater treatment and deodorization can be further improved by further improving the degradation efficiency of oils and fats, starch and proteins contained in wastewater.

Wastewater Treatment System

In one embodiment thereof, the present invention provides a wastewater treatment system provided with a biological treatment tank that biologically treats wastewater, wherein the previously described composition or support is contained in the aforementioned biological treatment tank.

Since the wastewater treatment system of the present embodiment has especially high degradation efficiency of oils and fats, starch, protein and other refractory components present in wastewater, treated water quality is high and there is little generation of foul odor and sludge. Consequently, the wastewater treatment system of the present embodiment can be preferably used to treat wastewater not only at food plants or processed food plants and the like, but also at factories, research facilities, barns or sewage treatment plants where wastewater is discharged that contains organic contaminants.

There are no particular limitations on the *Bacillus subtilis* var. *natto* used provided it is a microorganism classified as *Bacillus subtilis* var. *natto*. In addition, although there are no particular limitations on the content of *Bacillus subtilis* strain BN1001 and *Bacillus subtilis* var. *natto* in the aforementioned biological treatment tank provided they are contained to a degree that the effects of the invention of the present application are demonstrated, preferably *Bacillus subtilis* strain BN1001 is contained at 10% by weight to 90% by weight and *Bacillus subtilis* var. *natto* is contained at 10% by weight to 90% by weight, and more preferably *Bacillus subtilis* strain BN1001 is contained at 40% by weight to 60% by weight and *Bacillus subtilis* var. *natto* is contained at 60% by weight to 40% by weight in terms of the dry weight thereof based on the total weight of all microorganisms contained in the biological treatment tank.

In addition, it is also effective to add the aforementioned composition or support to the previously described grease trap. In this case, an aeration device is preferably added to the grease trap to supply oxygen required for growth of the group of microorganisms.

Although an ordinary grease trap is not used to biologically treat wastewater, this type of grease trap can be said to be a wastewater treatment system provided with a biological treatment tank that biologically treats wastewater.

As a result of adding the aforementioned composition or support to a grease trap, oil and fat that accumulate in the grease trap are no longer conspicuous, there is hardly any scum present, and generation of foul odor decreases. Consequently, work required to clean the grease trap can be simplified.

Wastewater Treating Method

In one embodiment thereof, the present invention provides a wastewater treating method that biologically treats wastewater, comprising a step for adding the previously described composition or support to the wastewater.

According to the wastewater treating method of the present embodiment, since the wastewater treating method of the present embodiment is able to degrade oils and fats, starch, protein and other refractory components present in wastewater with especially high efficiency, high treated water quality is obtained and there is little generation of foul odor and sludge. Consequently, the wastewater treating method of the present embodiment can be preferably used to treat wastewater not only at food plants or processed food plants, but also at factories, research facilities, barns or sewage treatment plants where wastewater is discharged that contains organic contaminants.

There are no particular limitations on the *Bacillus subtilis* var. *natto* used provided it is a microorganism classified as *Bacillus subtilis* var. *natto*. In addition, there are no particular limitations on the added amounts of *Bacillus subtilis* strain BN1001 and *Bacillus subtilis* var. *natto* provided they are added to a degree that the effects of the invention of the present application are demonstrated, and the added amounts thereof can be suitably adjusted.

In addition, a wastewater treating method in which the aforementioned composition or support is added to the previously described grease trap is also effective. In this case, an aeration device is preferably added to the grease trap to supply oxygen required for growth of the group of microorganisms.

Although an ordinary grease trap is not used to biologically treat wastewater, this type of grease trap can be said to biologically treat wastewater.

As a result of adding the aforementioned composition or support to a grease trap, oil and fat that accumulate in the grease trap are no longer conspicuous, there is hardly any scum present, and generation of foul odor decreases. Consequently, work required to clean the grease trap can be simplified.

Deodorization Method

In one embodiment thereof, the present invention provides a deodorization method comprising a step for contacting *Bacillus subtilis* strain BN1001 (deposited as Accession No. NITE BP-02608) and *Bacillus subtilis* var. *natto* with a malodorous source.

According to the deodorization method of the present invention, the deodorization method of the present invention is able to efficiently eliminate not only foul odors generated by wastewater treatment systems, but also by locations in the home or commercial facilities, such as the kitchen, food preparation area, lavatory, bathroom, laundry room or garbage collection sites, as well as in barns located on pig farms or chicken farms.

Contacting *Bacillus subtilis* strain BN1001 and *Bacillus subtilis* var. *natto* with a malodorous source refers to sprinkling a culture of these microorganisms or the aforementioned composition obtained by processing these microorganisms into the form of a powder or liquid at a location where the causative substance of a foul odor is present. As a result, these microorganisms are able to eliminate odor by efficiently degrading the causative substance of the foul odor or substances causing the generation thereof. Examples of substances causing a foul odor are the same as those previously listed.

Batch Wastewater Treating Method

In one embodiment thereof, the present invention provides a batch wastewater treating method comprising a wastewater introduction step for introducing wastewater into a biological treatment tank that biologically treats wastewater, an aeration step for aerating the introduced wastewater, a standing step for allowing the wastewater to stand undisturbed following aeration, and a discharge step for discharging the treated water after standing, wherein each of the wastewater introduction step, the aeration step, the standing step and the discharge step is repeated, and the biological treatment tank contains the previously described support.

A batch wastewater treating method refers to a method by which wastewater is treated while repeating cycles consisting of introduction of wastewater, aeration, standing (sedimentation) and discharge of treated water (supernatant) in a single biological treatment tank. Since suspended solids (SS) frequently float to the surface during the standing step, treated water is preferably discharged from beneath the water surface (between the sludge interface and water surface) instead of from the water surface.

In this batch wastewater treating method, denitrification effects attributable to denitrifying bacteria can be expected since an anaerobic state is created during introduction of wastewater and during standing, sludge settles favorably since the duration of settling time can be made to be long, and the structure of the device can be simplified since a single biological treatment tank serves as both an aeration tank and settling tank, thereby making this advantageous. In addition, since aeration time and standing time can be changed easily, wastewater treatment conditions can be easily adjusted to match changes in wastewater volume, water temperature and the like.

According to the batch wastewater treating method of the present embodiment, since the batch wastewater treating method of the present embodiment is able to degrade oils and fats, starch, protein and other refractory components present in wastewater with especially high efficiency, high treated water quality is obtained and there is little generation of foul odor and sludge. Consequently, the batch wastewater treating method of the present embodiment can be preferably used to treat wastewater not only at food plants or processed food plants, but also at factories, research facilities, barns or sewage treatment plants where wastewater is discharged that contains organic contaminants.

EXAMPLES

Although the following provides an explanation of the present invention through examples thereof, the present invention is not limited to the following examples.

Experimental Example 1

Comparison Between *Bacillus subtilis* strain BN1001 Alone and Mixture of *Bacillus subtilis* strain BN1001 and *Bacillus subtilis* var. *natto*

A comparison of properties was made between *Bacillus subtilis* strain BN1001 (deposited as Accession No. NITE BP-02608) alone and a mixture of *Bacillus subtilis* strain BN1001 and *Bacillus subtilis* var. *natto*.

(Comparison of Catalase Activity)

*Bacillus subtilis* strain BN1001 alone and a mixture of *Bacillus subtilis* strain BN1001 and *Bacillus subtilis* var. *natto* were respectively cultured using a medium having the composition shown in Table 1. Each culture broth was recovered in the logarithmic growth phase and bacterial concentration ($OD_{600}$) was adjusted to 0.5 using fresh medium.

TABLE 1

| | Water | 100 mL |
|---|---|---|
| Carbon source | Glucose | 0.4 g |
| Nitrogen sources | Yeast extract | 0.5 g |
| | Peptone | 0.1 g |
| Trace elements | Potassium chloride | 0.01 g |
| | Magnesium sulfate heptahydrate | 0.01 g |

Continuing, two test tubes were prepared containing 5 mL aliquots of 3% aqueous hydrogen peroxide solution, 1 mL of culture broth of the aforementioned *Bacillus subtilis* strain BN1001 alone was added to one of the test tubes, while 1 mL of culture broth of the aforementioned mixture of *Bacillus subtilis* strain BN1001 and *Bacillus subtilis* var. *natto* was added to the other test tube. As a result, oxygen bubbles formed due to decomposition of the hydrogen peroxide by catalase produced by the bacteria. FIG. 1 shows a photograph of the results of the catalase activity test. In the photograph, the test tube on the right side indicates the results for *Bacillus subtilis* strain BN1001 alone, while the test tube on the left side indicates the results for the mixture of *Bacillus subtilis* strain BN1001 and *Bacillus subtilis* var. *natto*.

As a result, the mixture of *Bacillus subtilis* strain BN1001 and *Bacillus subtilis* var. *natto* clearly demonstrated considerably higher catalase activity than *Bacillus subtilis* strain BN1001 alone.

In addition, this result indicates that *Bacillus subtilis* strain BN1001 alone and a mixture of *Bacillus subtilis* strain BN1001 and *Bacillus subtilis* var. *natto* have different bacteriological properties.

Comparison of Growth Rate 1.5% by weight of agar was added to the medium having the composition shown in the aforementioned Table 1 followed by solidifying in a Petri dish to prepare an agar medium.

In addition, *Bacillus subtilis* strain BN1001 alone and a mixture of *Bacillus subtilis* strain BN1001 and *Bacillus subtilis* var. *natto* were respectively cultured using the medium having the composition shown in Table 1. Each culture broth was recovered during the logarithmic growth phase and bacterial concentration ($OD_{600}$) was adjusted to 0.5 using fresh medium.

Figure 2:
FIG. 2 is a photograph of agar media six hours after culturing.

50 μL aliquots of each culture broth were inoculated into the aforementioned agar medium followed by culturing for 6 hours in an incubator at 30° C. to examine the degree of bacterial growth. FIG. 2 is a photograph showing the agar medium after culturing for 6 hours. In the photograph, the Petri dish on the left side indicates the results for *Bacillus subtilis* strain BN1001 alone, while the Petri dish on the right side indicates the results for the mixture of *Bacillus subtilis* strain BN1001 and *Bacillus subtilis* var. *natto*.

As a result, the mixture of *Bacillus subtilis* strain BN1001 and *Bacillus subtilis* var. *natto* clearly demonstrated a considerably faster growth rate in comparison with *Bacillus subtilis* strain BN1001 alone.

Comparison of Wastewater Treatment Capacity

Wastewater treatment capacity was compared using samples of wastewater discharged from a food plant engaged in the production of shellfish and kelp boiled in soy sauce.

First, *Bacillus subtilis* strain BN1001 alone and a mixture of *Bacillus subtilis* strain BN1001 and *Bacillus subtilis* var. *natto* were respectively cultured using the medium having the composition shown in the aforementioned Table 1. Each culture broth was recovered in the logarithmic growth phase and bacterial concentration ($OD_{600}$) was adjusted to 0.5 using fresh medium.

200 mL of the aforementioned wastewater were placed in two 500 mL Erlenmeyer flasks. 1 mL aliquots of each of the aforementioned culture broths were added to these Erlenmeyer flasks followed by stirring continuously using a magnetic stirrer at room temperature to carry out wastewater treatment.

The wastewater prior to wastewater treatment (untreated wastewater) and wastewater after subjecting to wastewater treatment for 48 hours were measured for pH, biological oxygen demand (BOD), and the amounts of n-hexane extracted substances (n-Hex). pH was measured in accordance with JIS K0102.12.1. BOD was measured in accordance with JIS K0102.21 and 32.3. The amount of n-hexane extracted substances was measured in accordance with the method described in Attached Table 4 of Environment Agency Notification No. 64 (Testing Methods relating to Wastewater Standards established by the Minister of the Environment based on the Provisions of Ministerial Ordinances Stipulating Wastewater Standards, promulgation date: Sep. 30, 1974).

The results are shown in Table 2. In Table 2, with regard to pH, the amount of the rise in pH is shown as an indicator of treatment rate. The pH of the untreated wastewater was 3.7. The pH rose by 1.5 to 5.2 as a result of treating the wastewater for 48 hours using *Bacillus subtilis* strain BN1001 alone. On the other hand, the pH rose by 3.1 to 6.8 as a result of treating the wastewater for 48 hours using the mixture of *Bacillus subtilis* strain BN1001 and *Bacillus subtilis* var. *natto*.

In addition, the BOD of the untreated wastewater was 2200 mg/L. BOD decreased to 730 mg/L as a result of treating the wastewater for 48 hours using *Bacillus subtilis* strain BN1001 alone. The treatment rate for BOD was 67%. On the other hand, BOD decreased to 450 mg/L as a result of treating the wastewater for 48 hours using the mixture of *Bacillus subtilis* strain BN1001 and *Bacillus subtilis* var. *natto*. The treatment rate for BOD was 80%.

In addition, the amount of n-hexane extracted substances of the untreated wastewater was 110 mg/L. The amount of n-hexane extracted substances decreased to 75 mg/L as a result of treating the wastewater for 48 hours using *Bacillus subtilis* strain BN1001. The treatment rate for n-hexane extracted substances was 32%. On the other hand, the amount of n-hexane extracted substances decreased to 30 mg/L as a result of treating the wastewater for 48 hours using the mixture of *Bacillus subtilis* strain BN1001 and *Bacillus subtilis* var. *natto*. The treatment rate for n-hexane extracted substances was 73%.

In this manner, the mixture of *Bacillus subtilis* strain BN1001 and *Bacillus subtilis* var. *natto* demonstrated considerably high wastewater treatment capacity for the rate of rise in pH, BOD treatment rate and n-hexane extracted substance treatment rate in comparison with *Bacillus subtilis* strain BN1001 alone.

TABLE 2

|  | *Bacillus subtilis* strain BN1001 alone | | | Mixture of *Bacillus subtilis* strain BN1001 and *Bacillus subtilis* var. *natto* | | |
| --- | --- | --- | --- | --- | --- | --- |
|  | pH | BOD (mg/L) | n-Hex (mg/L) | pH | BOD (mg/L) | n-Hex (mg/L) |
| Untreated wastewater | 3.7 | 2200 | 110 | 3.7 | 2200 | 110 |
| After treating for 48 hours | 5.2 | 730 | 75 | 6.8 | 450 | 30 |
| Treatment rate | +1.5 | 67% | 32% | +3.1 | 80% | 73% |

Other Properties

As a result of analyzing the bacteriological properties of the mixture of *Bacillus subtilis* strain BN1001 and *Bacillus subtilis* var. *natto*, the mixture of *Bacillus subtilis* strain BN1001 and *Bacillus subtilis* var. *natto* was clearly demonstrated to be able to grow at pH 3 to 9. In addition, the mixture of *Bacillus subtilis* strain BN1001 and *Bacillus subtilis* var. *natto* was clearly demonstrated to be able to grow at 10° C. to 50° C.

Experimental Example 2

Production of Composition and Support

Production Example 1

Liquid Composition 75 g of glucose, 105 g of beef extract, 150 g of peptone and 45 g of sodium chloride were dissolved in 15 L of tap water followed by adjusting the pH to 7.2 to prepare a medium. The prepared medium was placed in a 30 L jar fermenter and sterilized for 30 minutes at 121° C. Continuing, after cooling the sterilized medium, the medium was inoculated with pre-cultured *Bacillus subtilis* strain BN1001 (deposited as Accession No. NITE BP-02608) and *Bacillus subtilis* var. *natto* followed by aerated stir-culturing for 24 hours at 30° C. The resulting culture broth was used as a liquid composition.

Production Example 2

Powdered Composition (Support)

75 g of glucose, 105 g of beef extract, 150 g of peptone and 45 g of sodium chloride were dissolved in 15 L of tap water followed by adjusting the pH to 7.2 to prepare a medium. The prepared medium was sterilized for 30 minutes at 121° C. Continuing, the sterilized medium was cooled and inoculated with pre-cultured *Bacillus subtilis* strain BN1001 (deposited as Accession No. NITE BP-02608) and *Bacillus subtilis* var. *natto* followed by aerated stir-culturing for 24 hours at 30° C. Continuing, pearlite was added to and mixed with the resulting culture broth followed by additionally drying and crushing to obtain 1.3 kg of a powdered composition (support). The viable bacterial count contained in this composition (support) was $8 \times 10^9$ bacteria/g.

Production Example 3

Powdered Composition (Support)

500 g of corn stiplica adjusted to pH 7 and 300 g of tap water were added to 1 kg of commercially available soybean meal followed by mixing well to prepare a medium. The prepared medium was sterilized for 60 minutes at 121° C. Continuing, the sterilized medium was cooled and inoculated with pre-cultured *Bacillus subtilis* strain BN1001 (deposited as Accession No. NITE BP-02608) and *Bacillus subtilis* var. *natto* followed by aerated stir-culturing for 120 hours at 30° C. Continuing, calcium carbonate was added to and mixed with the resulting culture broth to obtain 1.6 kg of a powdered composition (support). The viable bacterial count contained in this composition (support) was $8 \times 10^9$ bacteria/g.

Production Example 4

Support

The powdered composition (support) of Production Example 2 was sealed in a plastic container to produce a ball-shaped support. The plastic container had a large number of holes of a size that allowed the powdered composition (support) to be retained inside the container while enabling wastewater and the support to make contact in the case of having added to a biological treatment tank.

Experimental Example 3

Comparison of Method of Present Invention with Activated Sludge Method

A biodegradability batch test was carried out for the method of the present invention and an activated sludge method using the biodegradable artificial raw water indicated in Table 3 as a sample followed by a comparison of the artificial raw water treatment capacities thereof.

TABLE 3

| Component | Amount |
|---|---|
| Soybean flour | 1 g |
| Sugar | 1 g |
| Powdered milk | 1 g |
| Powdered starch | 1 g |
| Water | 1000 mL |

First, an experiment was carried out using the method of the present invention. The composition of Production Example 1 was added to the artificial raw water having the composition shown in Table 3 to a concentration of 10 ppm and then introduced into a stationary contact aeration tank (capacity: 500 L).

The artificial raw water and treated water obtained 3 weeks later were measured for pH, biological oxygen demand (BOD), chemical oxygen demand (COD) and the amount of n-hexane extracted substances (n-Hex).

Next, an experiment was conducted using an activated sludge method. The artificial raw material having the composition shown in Table 3 was introduced into an activated sludge tank (capacity: 500 L).

Treated water obtained 3 weeks later was measured for pH, biological oxygen demand (BOD), chemical oxygen demand (COD) and the amount of n-hexane extracted substances (n-Hex).

The results are shown in Table 4. In Table 4, with regard to pH, the amount of the rise in pH is shown as an indicator of treatment rate. The pH of the artificial raw water was 5.5. As a result of treating for 3 weeks using the method of the present invention, the pH rose by 1.7 to 7.2. On the other hand, as a result of treating for 3 weeks using the activated sludge method, the pH rose by 1.5 to 7.0.

In addition, BOD of the artificial raw water was 2400 mg/L. As a result of treating for 3 weeks using the method of the present invention, BOD decreased to 41 mg/L. The BOD treatment rate was 98.3%. On the other hand, as a result of treating for 3 weeks using the activated sludge method, BOD decreased to 150 mg/L. The BOD treatment rate was 93.8%.

In addition, COD of the artificial raw water was 1600 mg/L. As a result of treating for 3 weeks using the method of the present invention, COD decreased to 130 mg/L. The COD treatment rate was 91.9%. On the other hand, as a result of treating for 3 weeks using the activated sludge method, COD decreased to 300 mg/L. The COD treatment rate was 81.3%.

In addition, the amount of n-hexane extracted substances of the artificial raw water was 280 mg/L. As a result of treating for 3 weeks using the method of the present invention, the amount of n-hexane extracted substances decreased to 5 mg/L. The n-hexane extracted substance treatment rate was 98.2%. On the other hand, as a result of treating for 3 weeks using the activated sludge method, the amount of n-hexane extracted substances decreased to 19 mg/L. The n-hexane extracted substance treatment rate was 93.2%.

In this manner, the method of the present invention demonstrated high artificial raw water treatment capacity for the rate of rise in pH, BOD treatment rate, COD treatment rate and n-hexane extracted substance treatment rate in comparison with the activated sludge method.

TABLE 4

|  | Artificial raw water | Following treatment with method of present invention | Treatment rate | Following treatment with activated sludge method | Treatment rate |
| --- | --- | --- | --- | --- | --- |
| pH | 5.5 | 7.2 | +1.7 | 7.0 | +1.5 |
| BOD (mg/mL) | 2400 | 41 | 98.3% | 150 | 93.8% |
| COD (mg/mL) | 1600 | 130 | 91.9% | 300 | 81.3% |
| n-Hex (mg/mL) | 280 | 5 | 98.2% | 19 | 93.2% |

Experimental Example 4

Application to Wastewater Treatment System

The previously described compositions or supports were applied to a wastewater treatment system of an actual food plant to examine wastewater treatment capacity.

Application Example 1

The composition of Production Example 1 was applied to a wastewater treatment system of a food plant engaged in the production of powdered seasonings.

Figure 3A:
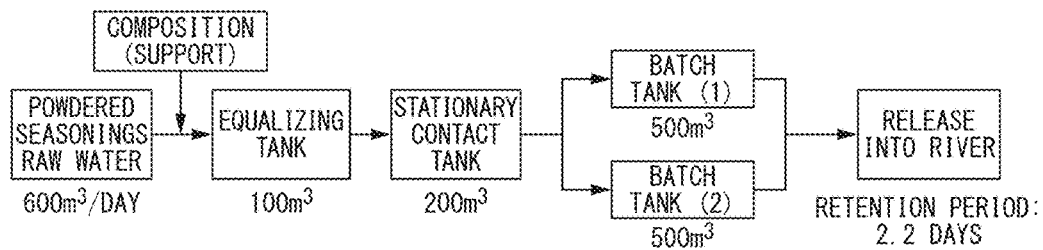
FIG. 3A shows a flow chart indicating an overview of a wastewater treatment system at a food plant where powdered seasonings are produced.

FIG. 3A shows a flow chart indicating an overview of the wastewater treatment system of the present application example. This plant discharged 600 m³ of wastewater per day. The configuration of the wastewater treatment system was as indicated below. First, the composition of Production Example 1 was added to untreated wastewater and introduced into an equalizing tank (capacity: 100 m³). Continuing, wastewater discharged from the equalizing tank was introduced into a stationary contact tank (capacity: 200 m³). The stationary contact tank contained *Bacillus subtilis* strain BN1001 and *Bacillus subtilis* var. *natto* retained on an immobilized support or support for a stationary bed system. Continuing, wastewater discharged from the stationary contact tank was introduced into two batch tanks (capacity: 500 m³ each). Continuing, treated water discharged from the batch tanks was released into a river. The wastewater retention period in this wastewater treatment system was 2.2 days.

The untreated wastewater and treated water were measured for pH, BOD, amount of n-hexane extracted substances (n-Hex), concentration of suspended solids (SS), chemical oxygen demand (COD), total nitrogen (T/N) and total phosphorous (T/P). BOD and amount of n-hexane extracted substances were measured in the same manner as previously described. SS was measured in accordance with the method described in Attached Table 8 of Environment Agency Notification No. 59 (Environmental Standards relating to Water Contamination, promulgation date: Dec. 28, 1971). COD was measured in accordance with JIS K0102.17. T/N was measured in accordance with JIS K0102.45.2. T/P was measured in accordance with JIS K0102.46.3.1.

The measured values for each parameter and treatment rates of wastewater treatment are shown in Table 5(a). In Table 5, with regard to pH, the amount of the rise in pH is shown as an indicator of treatment rate. As a result of applying the present composition, foul odor produced by the wastewater decreased in comparison with that prior to application. In addition, generation of excess sludge decreased. In addition, pH adjustment of the wastewater was not required.

Furthermore, similar results were also obtained following application of a liquid composition obtained by dissolving the powdered composition (support) of Production Example 2 or Production Example 3 in water.

Application Example 2

The composition of Production Example 1 was applied to a wastewater treatment system of a food plant engaged in the production of confections.

Figure 3B:
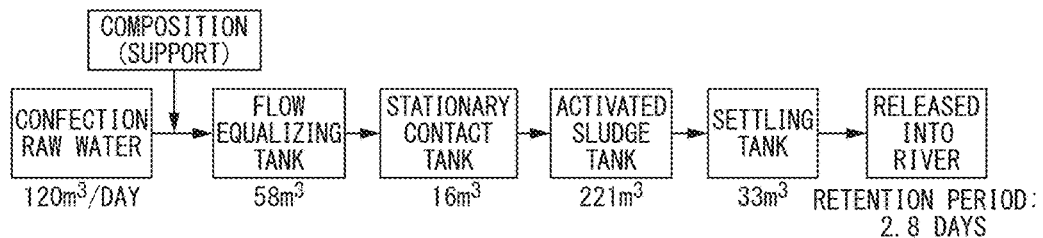
FIG. 3B shows a flow chart indicating an overview of a wastewater treatment system at a food plant where confections are produced.

FIG. 3B shows a flow chart indicating an overview of the wastewater treatment system of the present application example. This plant discharged 120 m³ of wastewater per day. The configuration of the wastewater treatment system was as indicated below. First, the composition of Production Example 1 was added to untreated wastewater and introduced into a flow equalizing tank (capacity: 58 m³). The flow equalizing tank contained *Bacillus subtilis* strain BN1001 and *Bacillus subtilis* var. *natto* retained on a sponge-like support or support for a fluidized bed system, and the support was allowed to flow inside the equalizing tank. Continuing, wastewater discharged from the flow equalizing tank was introduced into a stationary contact tank (capacity: 16 m³). The stationary contact tank contained *Bacillus subtilis* strain BN1001 and *Bacillus subtilis* var. *natto* retained on an immobilized support or a support for a stationary bed system. Continuing, wastewater discharged from the stationary contact tank was introduced into an activated sludge tank (capacity: 221 m³). Continuing, wastewater discharged from the activated sludge tank was introduced into a settling tank (capacity: 33 m³). Continuing, treated water discharged from the settling tank was released into a river. The wastewater retention period in this wastewater treatment system was 2.8 days.

The untreated wastewater and treated water were measured for pH, BOD, amount of n-hexane extracted substances (n-Hex), concentration of suspended solids (SS), chemical oxygen demand (COD), total nitrogen (T/N) and total phosphorous (T/P).

The measured values for each parameter and treatment rates of wastewater treatment are shown in Table 5(b). As a result of applying the present composition, foul odor produced by the wastewater decreased in comparison with that prior to application. In addition, generation of sludge decreased. In addition, pH adjustment of the wastewater was not required.

Furthermore, similar results were also obtained following application of a liquid composition obtained by dissolving the powdered composition (support) of Production Example 2 or Production Example 3 in water.

Application Example 3

The composition of Production Example 1 was applied to a wastewater treatment system of a food plant engaged in the production of beef and pork entrées.

Figure 3C:
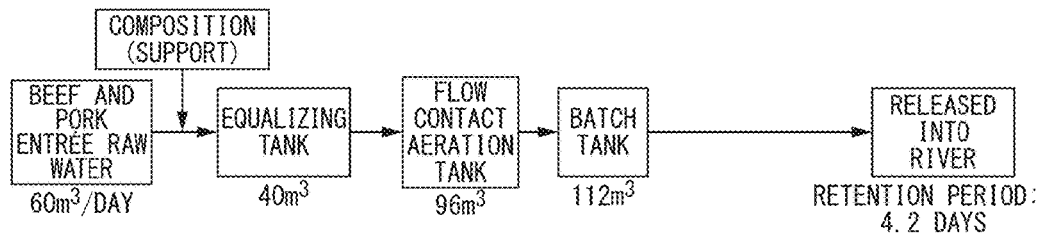
FIG. 3C shows a flow chart indicating an overview of a wastewater treatment system at a food plant where beef and pork entrées are produced.

FIG. 3C shows a flow chart indicating an overview of the wastewater treatment system of the present application example. This plant discharged 60 m³ of wastewater per day. The configuration of the wastewater treatment system was as indicated below. First, the composition of Production Example 1 was added to untreated wastewater and introduced into an equalizing tank (capacity: 40 m³). Continuing, wastewater discharged from the equalizing tank was introduced into a flow contact aeration tank (capacity: 96 m³). The flow contact aeration tank contained *Bacillus subtilis* strain BN1001 and *Bacillus subtilis* var. *natto* retained on a sponge-like support or support for a fluidized bed system, and the support was allowed to flow inside the flow contact aeration tank. Continuing, wastewater discharged from the flow contact aeration tank was introduced into a batch tank (capacity: 112 m³). Continuing, treated water discharged from the batch tank was released into a river. The wastewater retention period in this wastewater treatment system was 4.2 days.

The untreated wastewater and treated water were measured for pH, BOD, amount of n-hexane extracted substances (n-Hex), concentration of suspended solids (SS), chemical oxygen demand (COD), total nitrogen (T/N) and total phosphorous (T/P).

The measured values for each parameter and treatment rates of wastewater treatment are shown in Table 5(c). As a result of applying the present composition, foul odor produced by the wastewater decreased in comparison with that prior to application. In addition, generation of excess sludge decreased. In addition, pH adjustment of the wastewater was not required.

Furthermore, similar results were also obtained following application of a liquid composition obtained by dissolving the powdered composition (support) of Production Example 2 or Production Example 3 in water.

Application Example 4

The composition of Production Example 1 was applied to a wastewater treatment system of a food plant engaged in the production of Japanese entrées.

Figure 3D:
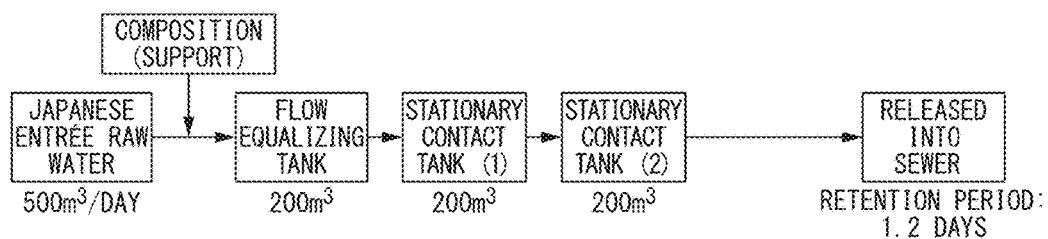
FIG. 3D shows a flow chart indicating an overview of a wastewater treatment system at a food plant where Japanese entrées are produced.

FIG. 3D shows a flow chart indicating an overview of the wastewater treatment system of the present application example. This plant discharged 500 m³ of wastewater per day. The configuration of the wastewater treatment system was as indicated below. First, the composition of Production Example 1 was added to untreated wastewater and introduced into a flow equalizing tank (capacity: 200 m³). The flow equalizing tank contained *Bacillus subtilis* strain BN1001 and *Bacillus subtilis* var. *natto* retained on a sponge-like support or support for a fluidized bed system, and the support was allowed to flow inside the equalizing tank. Continuing, wastewater discharged from the flow equalizing tank was introduced into a first stationary contact tank (capacity: 200 m³). The first stationary contact tank contained *Bacillus subtilis* strain BN1001 and *Bacillus subtilis* var. *natto* retained on an immobilized support or a support for a stationary bed system. Continuing, wastewater discharged from the first stationary contact tank was introduced into a second stationary contact tank (capacity: 200 m³). The configuration of the second stationary contact tank was the same as that of the first stationary contact tank. Continuing, treated water discharged from the second stationary contact tank was released into the sewer. The wastewater retention period in this wastewater treatment system was 1.2 days.

The untreated wastewater and treated water were measured for pH, BOD, amount of n-hexane extracted substances (n-Hex), concentration of suspended solids (SS), chemical oxygen demand (COD), total nitrogen (T/N) and total phosphorous (T/P).

The measured values for each parameter and treatment rates of wastewater treatment are shown in Table 5(d). As a result of applying the present composition, foul odor produced by the wastewater decreased in comparison with that prior to application. In addition, the amount of settled sludge decreased and sludge was not required to be transported out of the plant. In addition, pH adjustment of the wastewater was not required.

Furthermore, similar results were also obtained following application of a liquid composition obtained by dissolving the powdered composition (support) of Production Example 2 or Production Example 3 in water.

Application Example 5

The composition of Production Example 1 was applied to a wastewater treatment system of a cooked rice plant.

Figure 3E:
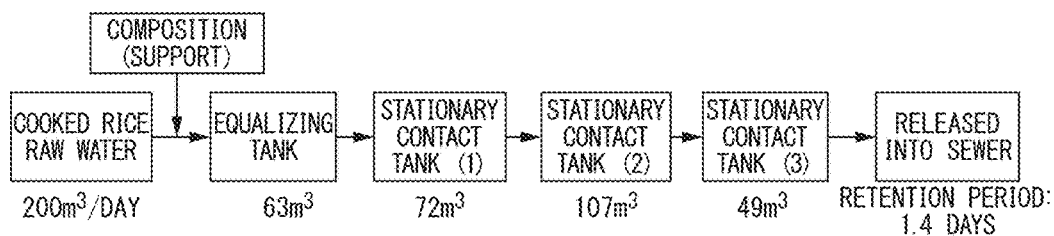
FIG. 3E shows a flow chart indicating an overview of a wastewater treatment system at a cooked rice plant.

FIG. 3E shows a flow chart indicating an overview of the wastewater treatment system of the present application example. This plant discharged 200 m³ of wastewater per day. The configuration of the wastewater treatment system was as indicated below. First, the composition of Production Example 1 was added to untreated wastewater and introduced into an equalizing tank (capacity: 63 m³). Continuing, wastewater discharged from the equalizing tank was introduced into a first stationary contact tank (capacity: 72 m³). The first stationary contact tank contained *Bacillus subtilis* strain BN1001 and *Bacillus subtilis* var. *natto* retained on an immobilized support or a support for a stationary bed system. Continuing, wastewater discharged from the first stationary contact tank was introduced into a second stationary contact tank (capacity: 107 m³). The configuration of the second stationary contact tank was the same as that of the first stationary contact tank. Continuing, wastewater discharged from the second stationary contact tank was introduced into a third stationary contact tank (capacity: 49 m³). The configuration of the third stationary contact tank was the same as that of the first stationary contact tank. Continuing, treated water discharged from the third stationary contact tank was released into the sewer. The wastewater retention period in this wastewater treatment system was 1.4 days.

The untreated wastewater and treated water were measured for pH, BOD, amount of n-hexane extracted substances (n-Hex), concentration of suspended solids (SS), total nitrogen (T/N) and total phosphorous (T/P).

The measured values for each parameter and treatment rates of wastewater treatment are shown in Table 5(e). As a result of applying the present composition, foul odor produced by the wastewater decreased in comparison with that prior to application. In addition, the amount of settled sludge decreased and sludge was not required to be transported out of the plant. In addition, pH adjustment of the wastewater was not required.

Furthermore, similar results were also obtained following application of a liquid composition obtained by dissolving the powdered composition (support) of Production Example 2 or Production Example 3 in water.

Application Example 6

The composition of Production Example 1 was applied to a wastewater treatment system of a cooked rice plant.

Figure 3F:
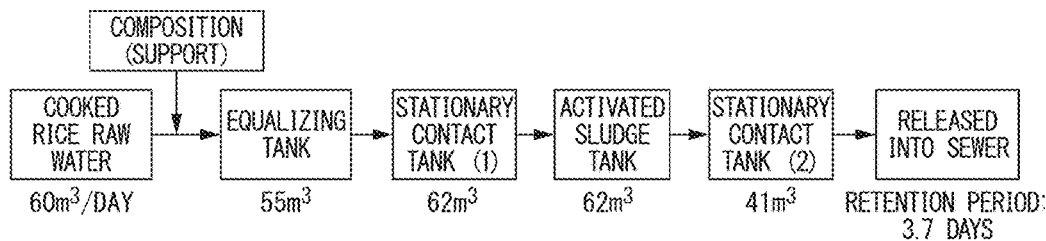
FIG. 3F shows a flow chart indicating an overview of a wastewater treatment system at a cooked rice plant.

FIG. 3F shows a flow chart indicating an overview of the wastewater treatment system of the present application example. This plant discharged 60 m³ of wastewater per day. The configuration of the wastewater treatment system was as indicated below. First, the composition of Production Example 1 was added to untreated wastewater and introduced into an equalizing tank (capacity: 55 m³). Continuing, wastewater discharged from the equalizing tank was introduced into a first stationary contact tank (capacity: 62 m³). The first stationary contact tank contained *Bacillus subtilis* strain BN1001 and *Bacillus subtilis* var. *natto* retained on an immobilized support or a support for a stationary bed system. Continuing, wastewater discharged from the first stationary contact tank was introduced into an activated sludge tank (capacity: 62 m³). Continuing, wastewater discharged from the activated sludge tank was discharged into a second stationary contact tank (capacity: 41 m³). The configuration of the second stationary contact tank was the same as that of the first stationary contact tank. Continuing, treated water discharged from the second stationary contact tank was released into the sewer. The wastewater retention period in this wastewater treatment system was 3.7 days.

The untreated wastewater and treated water were measured for pH, BOD, amount of n-hexane extracted substances (n-Hex), concentration of suspended solids (SS), chemical oxygen demand (COD), total nitrogen (T/N) and total phosphorous (T/P).

The measured values for each parameter and treatment rates of wastewater treatment are shown in Table 5(f). As a result of applying the present composition, foul odor produced by the wastewater decreased in comparison with that prior to application. In addition, the amount of settled sludge decreased and sludge was not required to be transported out of the plant. In addition, pH adjustment of the wastewater was not required.

Furthermore, similar results were also obtained following application of a liquid composition obtained by dissolving the powdered composition (support) of Production Example 2 or Production Example 3 in water.

Application Example 7

The composition of Production Example 1 was applied to a wastewater treatment system of a noodles plant.

Figure 3G:
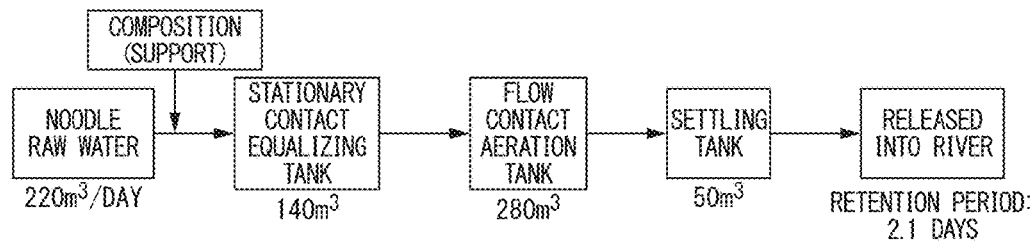
FIG. 3G shows a flow chart indicating an overview of a wastewater treatment system at a noodle plant.

FIG. 3G shows a flow chart indicating an overview of the wastewater treatment system of the present application example. This plant discharged 220 m³ of wastewater per day. The configuration of the wastewater treatment system was as indicated below. First, the composition of Production Example 1 was added to untreated wastewater and introduced into a stationary contact equalizing tank (capacity: 140 m³). The stationary contact equalizing tank contained *Bacillus subtilis* strain BN1001 and *Bacillus subtilis* var. *natto* retained on an immobilized support or support for a stationary bed system. Continuing, wastewater discharged from the stationary contact equalizing tank was introduced into a flow contact aeration tank (capacity: 280 m³). The flow contact aeration tank contained *Bacillus subtilis* strain BN1001 and *Bacillus subtilis* var. *natto* retained on a sponge-like support or a support for a fluidized bed system, and the support was allowed to flow inside the flow contact aeration tank. Continuing, wastewater discharged from the flow contact aeration tank was introduced into a settling tank (capacity: 50 m³). Continuing, treated water discharged from the settling tank was released into a river. The wastewater retention period in this wastewater treatment system was 2.1 days.

The untreated wastewater and treated water were measured for pH, BOD, amount of n-hexane extracted substances (n-Hex), concentration of suspended solids (SS), chemical oxygen demand (COD), total nitrogen (T/N) and total phosphorous (T/P).

The measured values for each parameter and treatment rates of wastewater treatment are shown in Table 5(g). As a result of applying the present composition, foul odor produced by the wastewater decreased in comparison with that prior to application. In addition, the amount of settled sludge decreased and sludge was not required to be transported out of the plant. In addition, pH adjustment of the wastewater was not required.

Furthermore, similar results were also obtained following application of a liquid composition obtained by dissolving the powdered composition (support) of Production Example 2 or Production Example 3 in water.

TABLE 5

| | Product | | pH | BOD (mg/L) | n-Hex (mg/L) | SS (mg/L) | COD (mg/L) | T/N (mg/L) | T/P (mg/L) | Released site | Discharged water volume (m³) | Retention time (days) |
|---|---|---|---|---|---|---|---|---|---|---|---|---|
| (a) | Powdered seasonings | Untreated wastewater | 5 | 3200 | 150 | 300 | 880 | 260 | 14 | River | 600 | 2.2 |
| | | Treated water | 6 | 36 | 1 | 37 | 58 | 41 | 1.2 | | | |
| | | Treatment rate | +1 | 98.9% | 99.3% | 87.7% | 93.4% | 84.2% | 91.4% | | | |
| (b) | Confections | Untreated wastewater | 5 | 570 | 74 | 140 | 240 | 10 | 0.43 | River | 120 | 2.8 |
| | | Treated water | 7 | 4.7 | 1 | 13 | 9.2 | 2.4 | 0.29 | | | |
| | | Treatment rate | +2 | 99.2% | 98.6% | 90.7% | 96.2% | 76.0% | 32.6% | | | |
| (c) | Beef and pork entrées | Untreated wastewater | 6 | 1400 | 33 | 1000 | 640 | 54 | 8.6 | River | 60 | 4.2 |
| | | Treated water | 7 | 19 | 2 | 21 | 28 | 5.3 | 0.72 | | | |
| | | Treatment rate | +1 | 98.6% | 93.9% | 97.9% | 95.6% | 90.2% | 91.6% | | | |
| (d) | Japanese entrées | Untreated wastewater | 4 | 1800 | 110 | 260 | 300 | 32 | 7.2 | Sewer | 500 | 1.2 |
| | | Treated water | 7 | 79 | 1 | 27 | 120 | 10 | 3.7 | | | |
| | | Treatment rate | +3 | 95.6% | 99.1% | 89.6% | 60.0% | 68.8% | 48.6% | | | |
| (e) | Cooked rice | Untreated wastewater | 7 | 2300 | 480 | 2100 | — | 60 | 33 | Sewer | 200 | 1.4 |
| | | Treated water | 7 | 180 | 17 | 180 | — | 35 | 18 | | | |
| | | Treatment rate | 0 | 92.1% | 96.4% | 91.4% | — | 41.6% | 45.4% | | | |
| (f) | Cooked rice | Untreated wastewater | 4 | 970 | 91 | 650 | 480 | 42 | 22 | Sewer | 60 | 3.7 |
| | | Treated water | 7 | 46 | 1 | 95 | 94 | 15 | 15 | | | |
| | | Treatment rate | +3 | 95.3% | 98.9% | 85.4% | 80.4% | 64.3% | 31.8% | | | |

TABLE 5-continued

| | Product | | pH | BOD (mg/L) | n-Hex (mg/L) | SS (mg/L) | COD (mg/L) | T/N (mg/L) | T/P (mg/L) | Released site | Discharged water volume (m³) | Retention time (days) |
|---|---|---|---|---|---|---|---|---|---|---|---|---|
| (g) | Noodles | Untreated wastewater | 5 | 1500 | 10 | 200 | 600 | 22 | 5 | River | 220 | 2.1 |
| | | Treated water | 7 | 2 | 1 | 4 | 9 | 1 | 0.3 | | | |
| | | Treatment rate | +2 | 99.9% | 90.0% | 98.0% | 98.5% | 95.5% | 94.0% | | | |

Experimental Example 5

Deodorization

Hydrogen sulfide was being generated by the wastewater treatment system of a restaurant and was causing a problem. Therefore, the composition of Production Example 1 and the support of Production Example 4 were jointly applied to this wastewater treatment system followed by measurement of changes in the concentration of the generated hydrogen sulfide.

Figure 4:
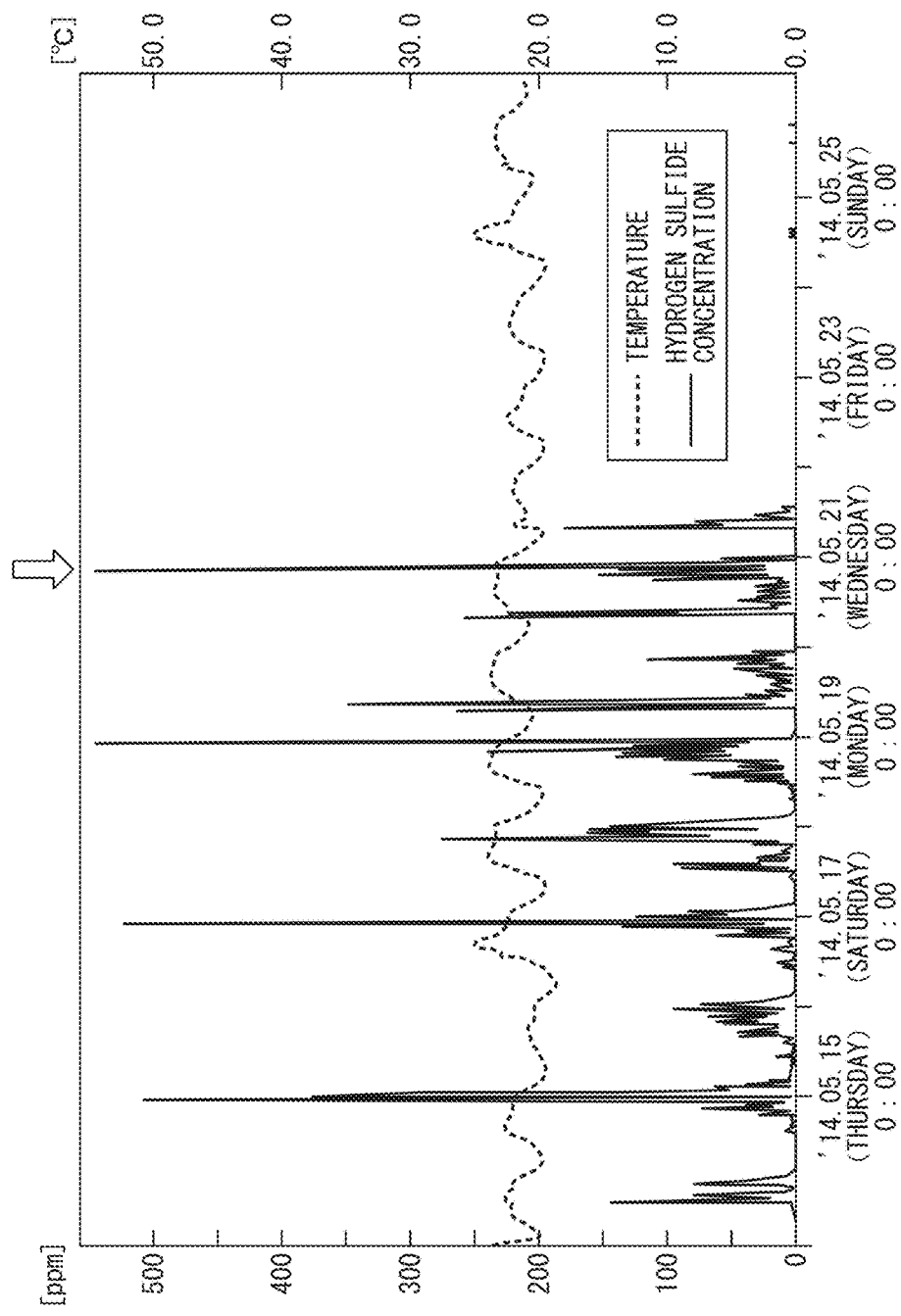
FIG. 4 shows a graph indicating changes in the concentration of hydrogen sulfide generated by a wastewater treatment system.

FIG. 4 shows a graph indicating changes in the concentration of hydrogen sulfide generated by this wastewater treatment system and changes in the temperature of a biological treatment tank of this wastewater treatment system. The arrow in FIG. 4 indicates the time when the composition of Production Example 1 and the support of Production Example 4 were jointly applied to this wastewater treatment system. The generation of hydrogen sulfide essentially discontinued about 8 hours after jointly applying the composition of Production Example 1 and the support of Production Example 4. This result indicates that a composition containing *Bacillus subtilis* strain BN1001 and *Bacillus subtilis* var. *natto* or a support having *Bacillus subtilis* strain BN1001 and *Bacillus subtilis* var. *natto* supported thereon is highly effective for deodorization.

INDUSTRIAL APPLICABILITY

According to the present invention, a composition can be provided that is capable of further improving the efficiency of wastewater treatment and deodorization by further improving the degradation efficiency of fats and oils, starch and protein. In addition, a support having a group of microorganisms supported thereon can be provided that is capable of further improving the efficiency of wastewater treatment and deodorization by further improving the degradation efficiency of fats and oils, starch and protein by adding to a biological treatment tank of a wastewater treatment system. Moreover, a wastewater treatment system having improved treatment capacity and a wastewater treating method having improved treatment capacity can be provided. In addition, a highly efficient deodorization method can be provided. Moreover, a batch wastewater treating method can be provided that demonstrates improved treatment capacity.

The invention claimed is:

1. A composition for treating wastewater containing as active ingredients thereof *Bacillus subtilis* strain NITE BP-02608 and *Bacillus subtilis* var. *natto*, and said composition further comprising a carrier.

2. The composition for treating wastewater according to claim 1, which is in the form of a powder.

3. The composition for treating wastewater according to claim 1, which is in the form of a liquid.

4. The composition for treating wastewater according to claim 1, which is for degrading fats and oils.

5. The composition for treating wastewater according to claim 1, which is for degrading starch.

6. The composition for treating wastewater according to claim 1, which is for degrading protein.

7. A wastewater treatment system provided with a biological treatment tank that biologically treats wastewater; wherein, the composition according to claim 1 is contained in the biological treatment tank.

8. A wastewater treating method that biologically treats wastewater, comprising a step for adding the composition according to claim 1 to the wastewater.

9. A support for treating wastewater having *Bacillus subtilis* strain NITE BP-02608 and *Bacillus subtilis* var. *natto* supported thereon.

10. A wastewater treatment system provided with a biological treatment tank that biologically treats wastewater; wherein, a support having *Bacillus subtilis* strain NITE BP-02608 and *Bacillus subtilis* var. *natto* supported thereon is contained in the biological treatment tank.

11. A wastewater treating method that biologically treats wastewater; comprising a step for adding a support having *Bacillus subtilis* strain NITE BP-02608 and *Bacillus subtilis* var. *natto* supported thereon to the wastewater.

12. A batch wastewater treating method, comprising:
a wastewater introduction step for introducing wastewater into a biological treatment tank that biologically treats wastewater,
an aeration step for aerating the introduced wastewater,
a standing step for allowing the wastewater to stand undisturbed following the aeration, and
a discharge step for discharging the treated water after the standing step; wherein,
each of the wastewater introduction step, the aeration step, the standing step and the discharge step is repeated, and
the biological treatment tank contains a support having *Bacillus subtilis* strain NITE BP-02608 and *Bacillus subtilis* var. *natto* supported thereon.

* * * * *

UNITED STATES PATENT AND TRADEMARK OFFICE
CERTIFICATE OF CORRECTION

PATENT NO. : 10,052,399 B2  
APPLICATION NO. : 15/505427  
DATED : August 21, 2018  
INVENTOR(S) : Makoto Takaya Page 1 of 1

It is certified that error appears in the above-identified patent and that said Letters Patent is hereby corrected as shown below:

On the Title Page

At item (57), Line 3, "BP-02608" should be -- BP-02608) --.

Signed and Sealed this  
Nineteenth Day of March, 2019

Andrei Iancu  
*Director of the United States Patent and Trademark Office*